(12) United States Patent
Dredla, IV

(10) Patent No.: US 7,959,014 B2
(45) Date of Patent: Jun. 14, 2011

(54) ANESTHESIA MASK STAND

(76) Inventor: Thomas J. Dredla, IV, Scottsbluff, NE (US)

( * ) Notice: Subject to any disclaimer, the term of this patent is extended or adjusted under 35 U.S.C. 154(b) by 126 days.

(21) Appl. No.: 12/289,658

(22) Filed: Oct. 31, 2008

(65) Prior Publication Data
US 2009/0146026 A1 Jun. 11, 2009

Related U.S. Application Data

(60) Provisional application No. 60/996,796, filed on Dec. 5, 2007.

(51) Int. Cl.
*A47F 7/00* (2006.01)
(52) U.S. Cl. .................. 211/13.1; 211/85.13; 248/127; 248/205.5
(58) Field of Classification Search ............... 211/85.18, 211/71.01, 13.1, 85.13, 60.1; 248/176.1, 248/127, 214, 117.2, 116, 206.2, 205.5, 146
See application file for complete search history.

(56) References Cited

U.S. PATENT DOCUMENTS

| | | | |
|---|---|---|---|
| 2,009,360 A | | 7/1935 | Koch |
| 2,642,248 A | * | 6/1953 | Semon ................... 248/205.9 |
| 3,210,816 A | * | 10/1965 | Clemons ................... 128/852 |
| 3,696,920 A | * | 10/1972 | Lahay ...................... 206/370 |
| 3,946,451 A | * | 3/1976 | Spann ........................ 5/650 |
| 4,114,241 A | * | 9/1978 | Bisping ..................... 403/188 |
| 4,341,300 A | | 7/1982 | Roy |
| 4,606,735 A | * | 8/1986 | Wilder et al. .............. 604/180 |
| 4,795,429 A | * | 1/1989 | Feldstein ................... 604/80 |
| 4,846,429 A | * | 7/1989 | Scheurer et al. .......... 248/205.8 |
| 4,971,271 A | * | 11/1990 | Sularz ....................... 248/68.1 |
| 5,343,875 A | * | 9/1994 | Chase ....................... 128/846 |
| D361,131 S | * | 8/1995 | Leopold .................... D24/199 |
| 5,485,931 A | * | 1/1996 | Barr, Jr. ................... 211/70.6 |
| 5,577,693 A | | 11/1996 | Corn |
| 5,643,217 A | * | 7/1997 | Dobkin ..................... 604/180 |
| 5,649,565 A | * | 7/1997 | Mulla ....................... 137/343 |
| 5,961,927 A | * | 10/1999 | Isaacs et al. ............... 422/564 |
| 6,345,873 B1 | * | 2/2002 | Kim .......................... 312/209 |
| 6,363,931 B1 | | 4/2002 | Dellenbusch |
| 6,629,615 B2 | * | 10/2003 | Kim .......................... 211/85.13 |
| 7,090,184 B2 | | 8/2006 | Tinker |
| D568,723 S | * | 5/2008 | Morgan ..................... D8/356 |
| 2003/0024891 A1 | * | 2/2003 | Diamond .................. 211/85.13 |
| 2004/0206711 A1 | * | 10/2004 | Hoftman ................... 211/85.13 |

FOREIGN PATENT DOCUMENTS
GB 2238710 A * 6/1991
* cited by examiner

*Primary Examiner* — Darnell M Jayne
*Assistant Examiner* — Patrick Hawn
(74) *Attorney, Agent, or Firm* — Wenderoth, Lind & Ponack, L.L.P.

(57) ABSTRACT

A mask stand for accommodating different size anesthesia masks when not attached to an anesthesia circuit or a patient's airway is provided. The mask stand includes a base; and a releasable securing means attached to a bottom surface of the base for securing the base to and releasing the base from any flat surface within an anesthesia environment. The base includes a first holding groove that extends along a top surface for receiving a first sized anesthesia mask; and a second holding groove that extends along the top surface for receiving a second sized anesthesia mask. The first and second holding grooves are positioned in a parallel configuration with respect to each other and are cylindrical in shape so as to accommodate a cylindrical portion of respective anesthesia masks.

11 Claims, 4 Drawing Sheets

ANESTHESIA MASK STAND

CROSS-REFERENCE TO RELATED APPLICATIONS

This application claims priority to Provisional Application Ser. No. 60/996,796 entitled "Mask Stand" filed on Dec. 5, 2007, the contents of which are fully incorporated herein by reference.

FIELD OF THE INVENTION

The invention relates to devices for securely holding different types of anesthesia masks when not attached to an anesthesia circuit or a patient's airway.

BACKGROUND OF THE INVENTION

Typically, during surgical procedures it is necessary to administer general anesthesia to patients, both young and old. In many instances, the anesthesia is delivered via a gas through an anesthesia mask that is applied over a patient's nose and mouth. Additionally, adult patients and child patients require different size anesthesia masks to effectively deliver the anesthesia. This requires the ability to be able to switch between different size anesthesia masks quickly and easily. Additionally, it is also necessary to be able to store anesthesia masks securely, safely and hygienically when they are not attached to the anesthesia circuit or the patient's airway.

For example, it is necessary to be able to conveniently store an adult anesthesia mask while administering anesthesia to a child (using a child anesthesia mask). However, the adult anesthesia mask should be stored such that it does not impede an anesthesia provider's ability to quickly and easily re-attach the adult anesthesia mask to the anesthesia circuit. Therefore, it would be advantageous to have an anesthesia mask stand that can safely, hygienically and securely accommodate different size anesthesia masks when the masks are not being attached to the anesthesia circuit or to a patient airway. Additionally, it would also be advantageous to have an anesthesia mask stand that can be conveniently located so different size anesthesia masks can quickly be found within an anesthesia environment; particularly if an anesthesia emergency arises.

SUMMARY OF THE INVENTION

An embodiment of the invention is directed to an improved mask stand for accommodating different size anesthesia masks when the anesthesia masks are not attached to an anesthesia circuit or a patient's airway. The mask stand comprises a wedge-shaped base; and a securing means attached to the bottom surface of the wedge-shaped base to secure the mask stand to any flat surface within an anesthesia environment. Additionally, the securing means is releasable such that the mask stand can be conveniently re-located within the anesthesia environment.

The securing means includes a plurality of uniformly sized vacuum or suction cups projecting outwardly from the bottom surface of the wedge-shaped base. The plurality of uniformly sized vacuum or suction cups are removably attached to the bottom surface of the wedge-shaped base and secure the bottom surface of the wedge-shaped base to the flat surface.

Additionally, the top surface of the wedge-shaped base includes a first holding groove that extends along the top surface of the wedge-shaped base for receiving a first sized anesthesia mask; and a second holding groove that extends along the top surface of the wedge-shaped base for receiving a second sized anesthesia mask. The first and second holding grooves are positioned in a parallel configuration with respect to each other, extend along a substantial portion of the top surface of the wedge-shaped base, and are cylindrical in shape.

The diameter of the first holding groove is larger than the diameter of the second holding groove such that the first holding groove is capable of receiving an adult or large anesthesia mask and the second holding groove is capable of receiving a child or small anesthesia mask. The wedge-shaped base and the first and second holding grooves are constructed from a flexible and resilient material such as rubber, rubber composite or other similar material.

The first holding groove secures a first sized anesthesia mask (e.g., adult mask) via a frictional force between an outer surface of a cylindrical portion of the first sized anesthesia mask and the inner diameter of the first holding groove when a downward force is applied to the mask stand. Similarly, the second holding groove secures a second sized anesthesia mask (e.g., child mask) via a frictional force between an outer surface of a cylindrical portion of the second sized anesthesia mask and the inner diameter of the second holding groove when a downward force is applied to the mask stand.

In an embodiment of the invention, the first sized anesthesia mask is secured within the mask stand when the second sized anesthesia mask is removed from the mask stand, and the second sized anesthesia mask is secured within the mask stand when the first sized anesthesia mask is removed from the mask stand. However, it is also contemplated that two or more anesthesia masks can be accommodated by the mask stand at the same time.

Additionally, the first sized and second sized anesthesia masks can be removed from their respective holding grooves in the mask stand by exerting an upward force on the anesthesia masks. Additional features and advantages are described herein, and will be apparent from, the following detailed description of the invention and the figures.

DETAILED DESCRIPTION OF THE INVENTION

Figure 1:
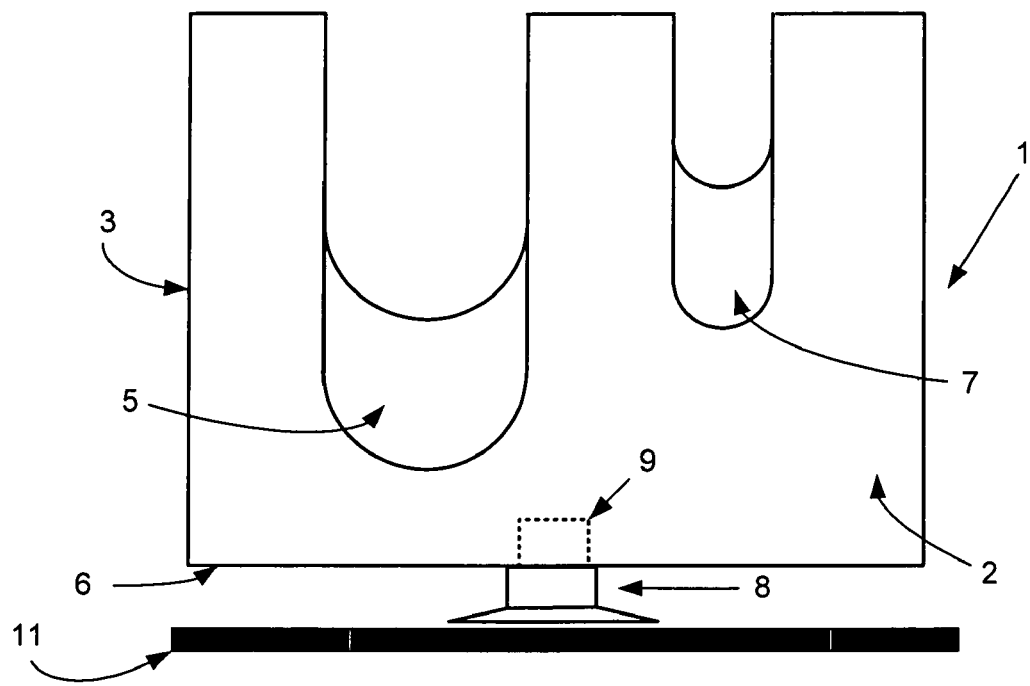
FIG. 1 is a front view of the mask stand in accordance with an embodiment of the invention.
Figure 2:
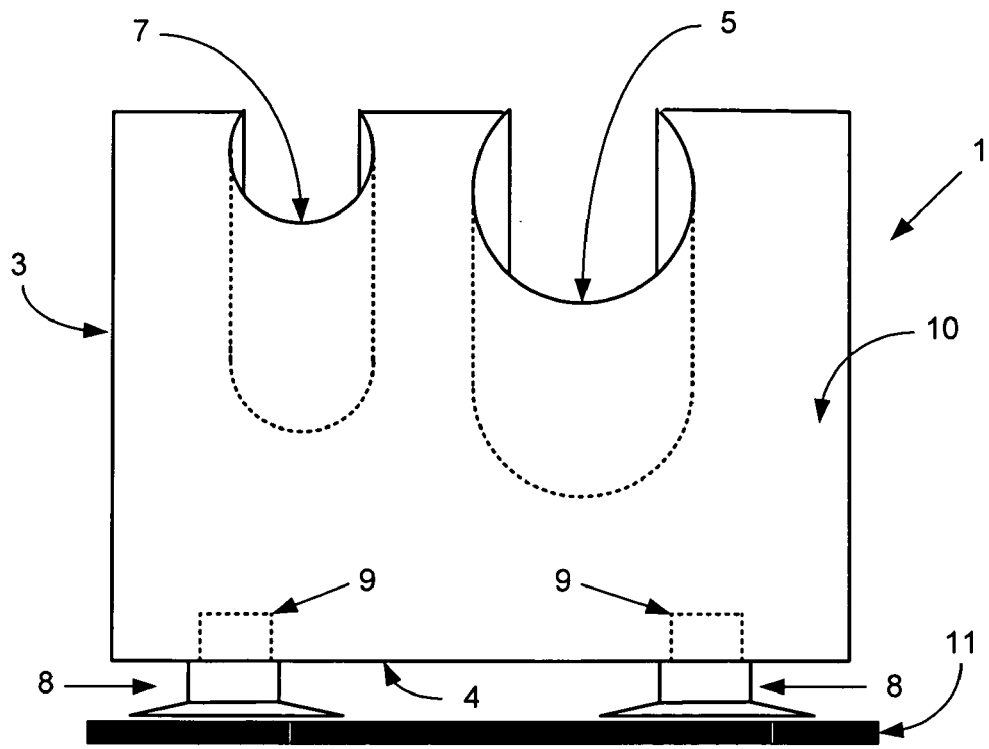
FIG. 2 is a rear view of the mask stand illustrated in FIG. 1.

FIGS. 1 and 2 illustrate respectively a front view and rear view of the mask stand in accordance with an embodiment of the invention. The mask stand 1 includes a wedge-shaped base 3 with a securing means 8 on a bottom surface 4 for securing the mask stand 1 any flat surface 11 within an anesthesia environment. A top surface 2 includes a first holding groove 5 and a second holding groove 7 for accommodating different size anesthesia masks (not shown) when the anesthesia masks are not attached to an anesthesia circuit or a patient's airway. For example, the first holding groove 5 that extends along the top surface 2 of the wedge-shaped base 3 receives a first sized anesthesia mask (not shown); and the second holding groove 7 that extends along the top surface 2 of the wedge-shaped base 3 receives a second sized anesthesia mask (not shown). The first and second holding grooves 5, 7 are positioned in a parallel configuration with respect to each other, and extend from the top of the back surface 10 toward the front 6 of the wedge-shaped base 3. As illustrated in FIGS. 1 and 2, the first and second holding grooves 5, 7 extend through the back surface 10 and occupy a substantial portion of the top surface 2.

The diameter of the first holding groove 5 is larger than the diameter of the second holding groove 7 so that the first holding groove 5 is capable of receiving an adult (e.g., large) anesthesia mask and the second holding groove 7 is capable of receiving a child (e.g., small) anesthesia mask. For example, the inside diameter of the first holding groove 5 is about 1.1 inches and the inside diameter of the second holding groove 7 is about 0.6 inches in diameter. However, the inside diameters of the first and second holding grooves 5, 7 are not limited to these sizes and may vary depending on the size of the anesthesia masks that need to be accommodated in the mask stand 1.

The wedge-shaped base 3 and the first and second holding grooves 5, 7 are constructed from a flexible and resilient material such as rubber, rubber composite or other similar material. The first holding groove 5 secures the first sized anesthesia mask via a frictional force between an outer surface of a cylindrical portion of the first sized anesthesia mask and an inner diameter of the first holding groove 5. Similarly, the second holding groove 7 secures the second sized anesthesia mask via a frictional force between an outer surface of a cylindrical portion of the second sized anesthesia mask and an inner diameter of the second holding groove 7. The details of how the different anesthesia masks are accommodated by the mask stand 1 are discussed in more detail with reference to FIGS. 7A and 7B.

The securing means 8 includes a plurality of uniformly sized vacuum or suction cups projecting outwardly from the bottom surface 4 of the wedge-shaped base 3. The vacuum or suction cups are constructed from rubber, rubber composite or other similar material. Therefore, the securing means 8 can be attached to the bottom surface 4 of the wedge-shaped base 3 for releasably securing the mask stand 1 to virtually any flat surface 11. For example, the securing means 8 can securely attach the wedge-shaped base 3 to a flat surface 11 by exerting a downward force on the wedge-shaped base 3, thereby creating a vacuum seal between the securing means 8 and the flat surface 11. The securing means 8 can also be released or disengaged from the flat surface 11 by exerting an upward force on the wedge-shaped base 3, thereby breaking the vacuum seal between the securing means 8 and the flat surface 11.

Figure 3:
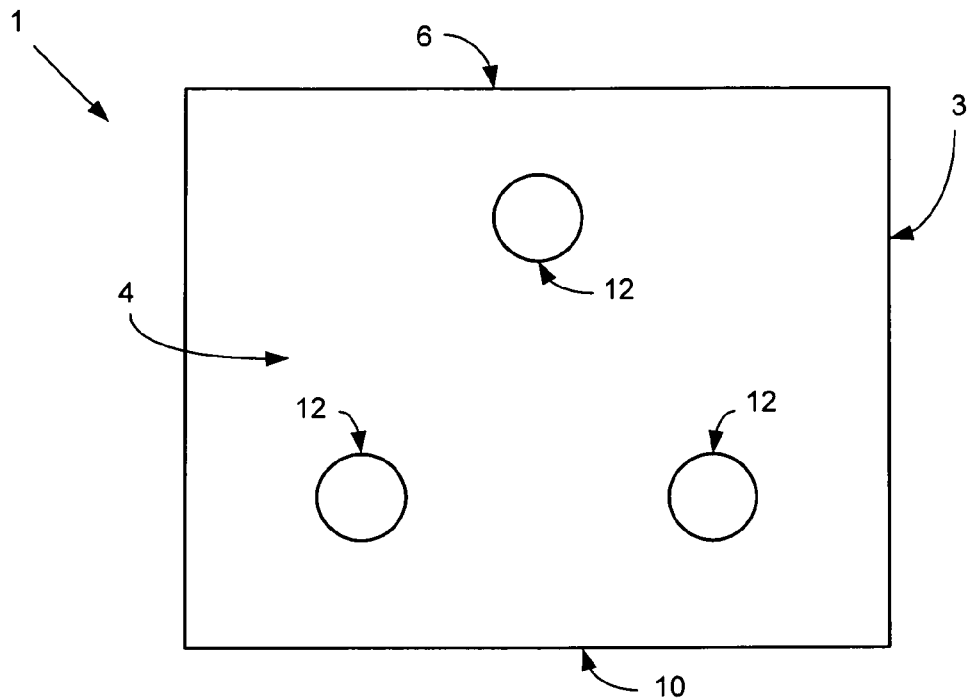
FIG. 3 is bottom view of the mask stand in accordance with an embodiment of the invention.
Figure 4:
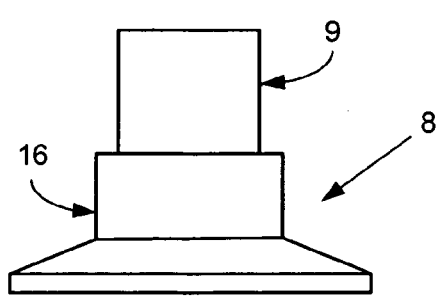
FIG. 4 is a side view of a vacuum or suction cup in accordance with an embodiment of the present invention.
Figure 5:
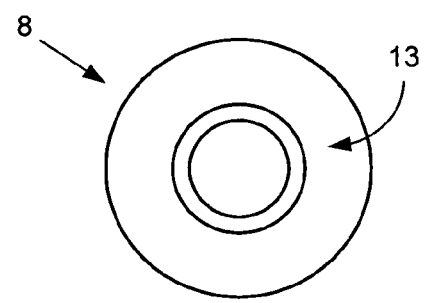
FIG. 5 is a bottom view of the vacuum or suction cup illustrated in FIG. 4.

FIG. 3 illustrates the bottom view of the wedged-shaped base 3 of the mask stand 1 in accordance with an embodiment of the invention. Additionally, FIGS. 4 and 5 illustrate respectively a side view and a bottom view of the securing means 8 in accordance with an embodiment of the invention. The bottom surface 4 of the wedge-shaped base includes a plurality of receiving holes 12 that receive an insert portion 9 of the securing means 8. The insert portion 9 extends into the receiving hole 12 until the bottom surface 4 comes into contact with a flange portion 16 of the securing means 8.

The securing means 8 can also be constructed of rubber, rubber composite or other similar material, and the insert portion 9 is secured within the receiving hole 12 using an adhesive or the like. Additionally, the securing means 8 can be replaced when they are worn or fail to provide a tight vacuum seal with respect to the flat surface 11. As seen in FIG. 3, a single receiving hole 12 is located proximate to the front 6 of the wedge-shaped base 3 of the mask stand 1; and two receiving holes are uniformly spaced proximate to the back 10 of the wedge-shaped base 3 of the mask stand 1.

The securing means 8 can securely attach the wedge-shaped base 3 to the flat surface 11 by exerting a downward force on the wedge-shaped base 3, thereby creating a vacuum seal between the inner surface 13 of the securing means 8 and the flat surface 11. The securing means 8 can also be released by exerting an upward force on the wedge-shaped base 3, thereby breaking the vacuum seal between the inner surface 13 of securing means 8 and the flat surface 11

Figure 6A:
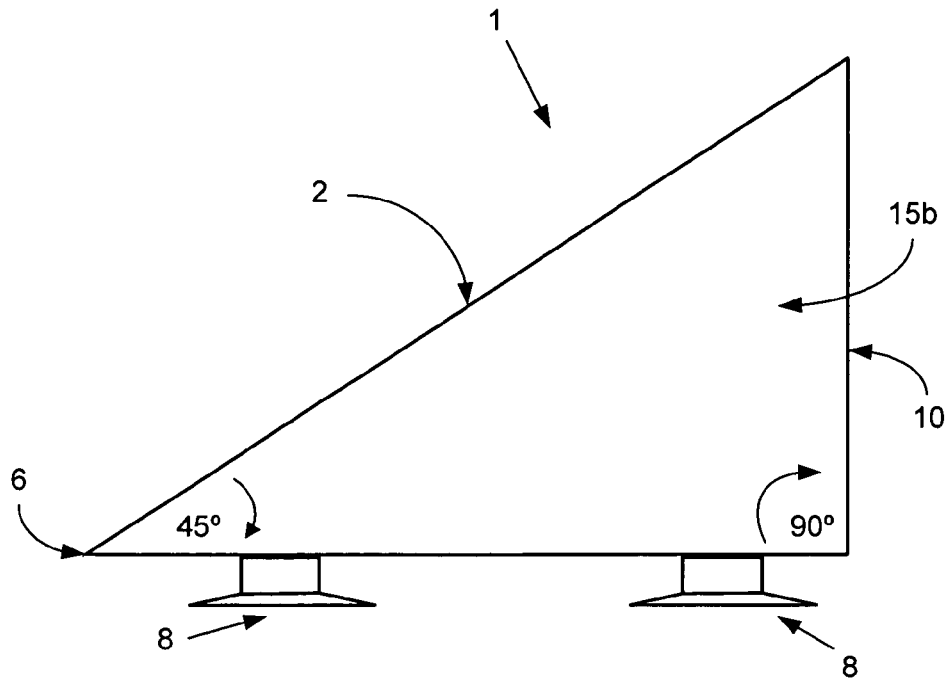
FIGS. 6A and 6B are side views of the mask stand in accordance with an embodiment of the present invention.
Figure 6B:
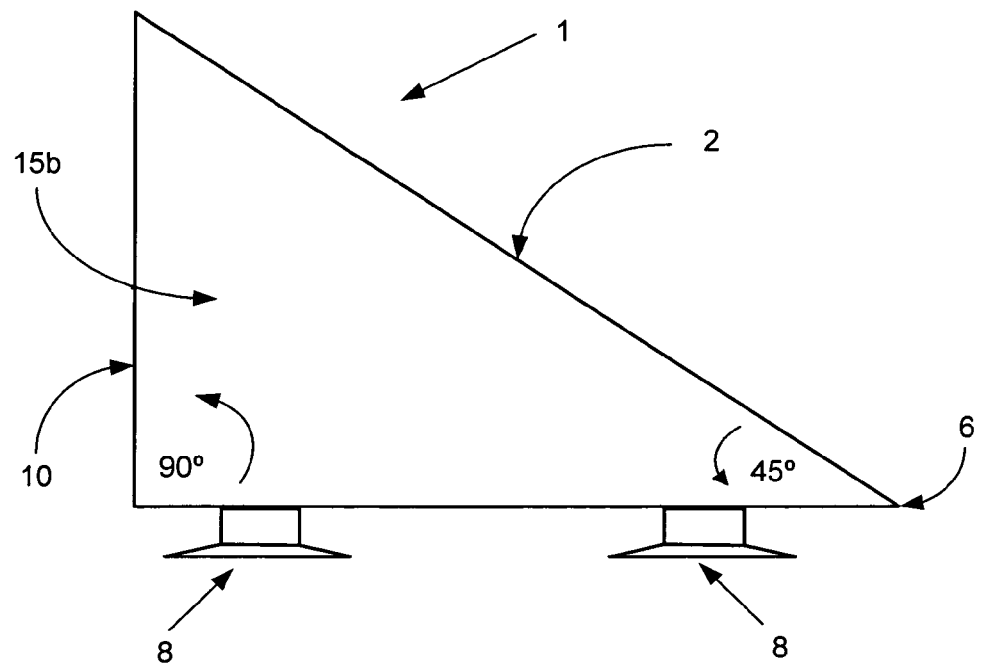

FIGS. 6A and 6B are side views of the mask stand in accordance with an embodiment of the present invention. FIG. 6A illustrates a first side 15*a* of the wedge-shaped base 3 and FIG. 6B illustrates the opposite second side 15*b* of the wedge-shaped base 3. The wedge-shape of the mask stand 1 is formed by the top surface 2 and the bottom surface 4 forming a 45 degree angle with respect to each other, and the rear surface 10 and the back surface 4 forming a 90 degree angle with respect to each other.

It should understood by one of ordinary skill in the art that the mask stand is not limited to a wedge-shaped base, and the base can be constructed as a different shape, such as a square, rectangle or the like. As long the shape of the mask stand is sufficient to accommodate the holding grooves for receiving and securing the different types of anesthesia masks.

Each side view (in FIGS. 6A and 6B) also illustrates the securing means 8 located on the bottom surface of the wedge-shaped base 3. Specifically, the two side views illustrate the single securing means 8 within the receiving hole 12 proximate the front 6 of the wedge-shaped base 3 and the securing means 8 within one of the two receiving holes 12 proximate to the back 10 of the wedge-shaped base 3.

Figure 7A:
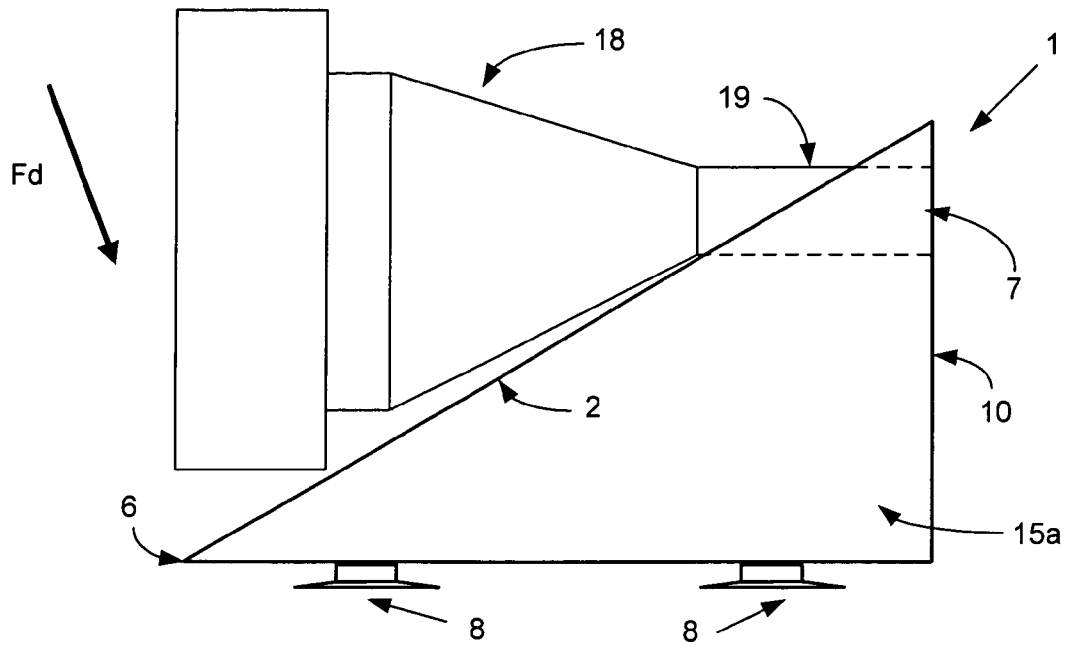
FIGS. 7A and 7B illustrate a method of using the mask stand to accommodate an anesthesia mask in accordance with an embodiment of the present invention.
Figure 7B:
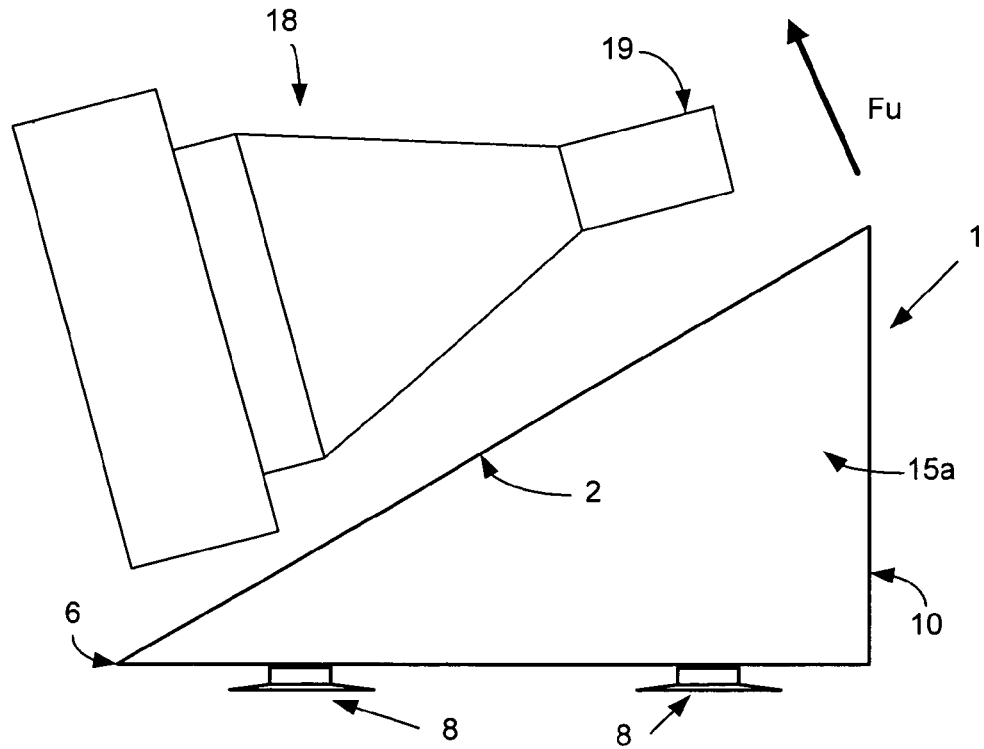

FIGS. 7A and 7B illustrate a method of using the mask stand to accommodate an anesthesia mask in accordance with an embodiment of the present invention. For ease of explanation, FIGS. 7A and 7B illustrate securing and removing a child or small anesthesia mask 18 with respect to the smaller diameter holding groove 7 of the mask stand 1. Additionally, the anesthesia mask 18 is illustrated in FIG. 7A as being secured with the majority of the anesthesia mask resting on the top surface 2 of the mask stand 1.

However, one of ordinary skill in the art would understand that the same method can be performed to secure and remove an adult or large anesthesia mask with respect to the larger diameter holding groove 5 of the mask stand 1. Additionally, the anesthesia mask can also be secured with the majority of the anesthesia mask 18 extending off the back 10 of the mask stand 1.

In FIG. 7A, when the anesthesia mask 18 is removed from the anesthesia circuit, an outer surface of a cylindrical portion 19 of the anesthesia mask 18 can be received within an inner diameter of the second holding groove 7 such that the anesthesia mask 18 is secured to the mask stand 1 by the frictional force between the outer surface of a cylindrical portion 19 and the inner diameter of the second holding groove 7 when a downward force Fd is exerted on the mask stand 1.

In FIG. 7B, the first sized anesthesia mask 18 can be removed the second holding groove 5 in the mask stand 1 by exerting an upward force Fu on the anesthesia mask 18 to thereby disengage the frictional force between the outer surface of a cylindrical portion 19 and the inner diameter of second holding groove 5.

It is contemplated in an embodiment of the invention that the first sized anesthesia mask is secured within the mask stand 1 when the second sized anesthesia mask is removed from the mask stand 1, and the second sized anesthesia mask is secured within the mask stand when the first sized anesthesia mask is removed from the mask stand 1. However, it should be understood by one of ordinary skill in the art that the mask stand 1 can be easily modified to accommodate two or more different sized anesthesia mask at different times or simultaneously.

It should be understood that various changes and modifications to the preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A mask stand for accommodating different size anesthesia masks when not attached to an anesthesia circuit or a patient's airway, the mask stand comprising:
    a base, the base being wedged-shaped;
    a releasable securing means attached to a bottom surface of said base for securing said base to and releasing said base from any flat surface within an anesthesia environment;
    a first holding groove extending along a top surface of said base for receiving a first sized anesthesia mask; and
    a second holding groove also extending along the top surface of said base for receiving a second sized anesthesia mask,
    wherein said first holding groove and said second holding groove are positioned in a parallel configuration with respect to each other,
    each of said first and second holding grooves includes a front portion and a back portion, the front portion gradually decreasing in depth so as to terminate respective first and second holding grooves at one end without extending an entire length of the top surface of said base, and
    a depth of the front portion of the respective first and second holding grooves is less than a depth of the back portion of the respective first and second holding grooves wherein a back surface of said base and the bottom surface of said base form a 45 degree angle with respect to one another.

2. The mask stand of claim 1, wherein a diameter of said first holding groove is larger than a diameter of said second holding groove.

3. The mask stand of claim 2, wherein said first holding groove is for receiving an adult anesthesia mask and said second holding groove is for receiving a child anesthesia mask.

4. The mask stand of claim 1, wherein said first holding groove is about 1.1 inches in diameter and said second holding groove is about 0.6 inches in diameter.

5. The mask stand of claim 1, wherein said base and said first and second holding grooves are constructed from a flexible and resilient rubber or rubber composite material.

6. The mask stand of claim 1, wherein said releasable securing means includes a plurality of uniformly sized vacuum or suction cups projecting outwardly from a bottom surface of said base.

7. The mask stand of claim 6, wherein the plurality of uniformly sized vacuum or suction cups are removably attached to the bottom surface of said base.

8. The mask stand of claim 1, wherein said first holding groove and said second holding groove extend along a substantial portion of the top surface of said base.

9. The mask stand of claim 1, wherein said first holding groove and said second holding groove are substantially cylindrical in shape.

10. The mask stand of claim 8, wherein said first holding groove secures the first sized anesthesia mask via a frictional force between an outer surface of a cylindrical portion of the first sized anesthesia mask and an inner diameter of said first holding groove.

11. The mask stand of claim 8, wherein said second holding groove secures the second sized anesthesia mask via a frictional force between an outer surface of a cylindrical portion of the second sized anesthesia mask and an inner diameter of said second holding groove.

* * * * *